United States Patent [19]

Rapoport et al.

[11] Patent Number: 5,322,942

[45] Date of Patent: Jun. 21, 1994

[54] SYNTHESIS OF OPTICALLY ACTIVE LACTONES FROM L-ASPARTIC ACID AND INTERMEDIATES THEREOF

[75] Inventors: Henry Rapoport, Berkeley, Calif.; Jeffrey M. Dener, King of Prussia, Pa.; Lin-hau Zhang, Albany, Calif.

[73] Assignee: Regents of the University of California, Oakland, Calif.

[21] Appl. No.: 709,373

[22] Filed: Jun. 3, 1991

[51] Int. Cl.⁵ .................. C07D 239/20; C07D 307/33
[52] U.S. Cl. .................................... 544/297; 546/283; 548/517; 549/295; 549/322; 549/323
[58] Field of Search ...................... 549/295, 322, 323; 548/336, 517; 546/283; 544/297

[56] References Cited

U.S. PATENT DOCUMENTS 4,977,172  12/1990  Johnson et al. ..................... 514/374

FOREIGN PATENT DOCUMENTS 0436851  7/1991  European Pat. Off. .

OTHER PUBLICATIONS

Jensen et al., "Preparation of *tert*-Butylmaleic Acid and its Di-*tert*-butyl Ester," *Acta Chemica Scandinavica*, vol. 21, No. 7 (1967), pp. 1963-1965.

Isaev et al., "Stereochemistry of the Chloroarylation of Fumaric and Maleic Acid Esters," *Chemical Abstracts*, vol. 78, No. 7 (1973), Abstract No. 42694v, p. 424.

Isaev et al., "Stereochemistry of Dehydrochlorination of 3-phenyl-2-chlorosuccinic Acid Esters," *Chemical Abstracts*, vol. 78, No. 15 (1973), Abstract No. 97039r, p. 426.

Oka et al., "Preparation of Dibenylbutanediol and Dibenyltetrahydrofuran Derivatives as Immunosuppressants," *Chemical Abstracts*, vol. 114, No. 3 (1991) Abstract No. 23554v, p. 665.

Minami et al., "Generation of the Enolate of Succinic Anhydride in the Presence of Carbonyl Compounds," *Tetrahedron Letters*, No. 17 (1977), pp. 1423-1424.

Compagnone et al., *J. Org. Chem.*, 51:10, 1713 (1986).
Link, *Helv. Chem. Acta*, 55, 1053 (1972).
Noordan, *Rec. J. R. Neth. Chem. Soc.*, 100, 441 (1981).
Wolf et al., *J. Org. Chem.*, 54, 3164-3173 (1989).

*Primary Examiner*—C. Warren Ivy
*Assistant Examiner*—A. Owens
*Attorney, Agent, or Firm*—Majestic, Parsons, Siebert & Hsue

[57] ABSTRACT

Optically active lactones are described, such as an intermediate lactone having the formula

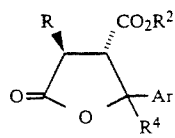

VIa where R and $R^2$ are each independently alkyl with 1 to 6 carbon atoms, cycloalkyl with 6 to 10 carbon atoms, aryl with 6 to 10 carbon atoms, or arylalkyl with 7 to 19 carbon atoms, $R^4$ is H or $C_{1-6}$ alkyl, and Ar is a homo- or heteroaromatic ring with 5 or 6 ring atoms being optionally substituted by $C_{1-6}$ alkyl or alkoxy groups, halogen atoms, cyano or nitro groups. Such optically active, intermediate lactones are prepared from L-aspartic acid, and can be readily converted to (+)-pilocarpine and its analogues by hydrolysis, reduction, and hydrogenation, such as to an optically active lactone having the formula

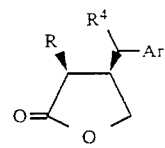

VIII which is (+)-pilocarpine when R is ethyl, $R^4$ is H, and Ar is 1-methylimidazol-5-yl.

16 Claims, No Drawings

SYNTHESIS OF OPTICALLY ACTIVE LACTONES FROM L-ASPARTIC ACID AND INTERMEDIATES THEREOF

FIELD OF THE INVENTION

The present invention relates generally to the synthesis of optically active lactones, and more particularly relates to the synthesis of compounds that are analogues of (+)-pilocarpine from L-aspartic acid through certain key intermediates. Thus, these intermediate compounds are important for the manufacture of therapeutically useful compounds.

BACKGROUND OF THE INVENTION (+)-Pilocarpine, the most important imidazole alkaloid, has been for many years the focus of much attention because of its extensive pharmacological properties. These include diaphoretic effects, stimulation of the parasympathetic system, miotic action, and particularly applications in ophthalmology. Pilocarpine is currently the drug of choice for treatment of narrow and wide angle glaucoma because it decreases the intraocular pressure and can be administered for long periods without side effects. Pilocarpine along with its epimer isopilocarpine was first isolated in 1875 from various species of Pilocarpus plants belonging to the Rutaceae family. The structure and stereochemistry of this alkaloid, proposed in 1900, was later confirmed in degradation studies, X-ray analysis, and several syntheses.

Earlier syntheses of (+)-pilocarpine were based on the formation of the lactone ring at an early stage followed by various group transformation and construction of the imidazole ring in the final stages. These syntheses suffered from the burden of many steps, low yields, lack of stereoselectivity, and mixtures of N-methylimidazole regiosiomers. A later approach to (+)-pilocarpine was based on using a preformed imidazole nucleus and building the lactone at a subsequent stage. However, the reported yield was less than 1%. Link, Helv. Chim. Acta 55, 1053 (1972). More recently a synthesis of (+)-pilocarpine starting with L-histidine was reported. Noordam, Rec. J.R. Neth. Chem. Soc., 100, 441 (1981). This synthesis is based on regioselective methylation of L-histidine, alkylation of the a-carbon with an ethyl malonate, and decarboxylation and formation of the lactone. In this last route the alkylation and decarboxylation steps occurred with limited stereochemical control, resulting in a mixture of diastereoisomeric products.

A chirospecific synthesis of (+)-pilocarpine using D-methionine or D-2-aminobutanol as chiral educt has been reported. Compagnone and Rapoport, J. Org. Chem., 51:10, 1713 (1986). However, the yield is reduced because (+)-pilocarpine is obtained through epimerization of (+)-isopilocarpine, and the epimer mixture must be separated.

J. Wolf and H. Rapoport describe the synthesis of certain dipeptide analogues starting from L-aspartic acid in the Journal of Organic Chemistry, 54, 3164–3173 (1989). However, the compound they describe as compound 28 (which is of interest for the present invention) gave the desired diastereomer in a ratio of 3.5:1 (with a yield of 78%) and included several impurities that had to be separated. Such a diastereomer ratio is impractically low for use in a commercially acceptable synthesis towards (+)-pilocarpine or its analogues.

An analogue of (+)-pilocarpine, (2)-3-ethyl-4-[(1-methyl-1H-imidazol-5-yl)methyl]-2-oxazolidinone, is described in U.S. Pat. No. 4,977,172, issued Dec. 11, 1990, which describes use of said pilocarpine analogue for treating the symptoms of cognitive decline in an elderly patient (e.g. Alzheimer's disease). This analogue is not formed from an L-aspartic acid precursor.

SUMMARY OF THE INVENTION

It is an object of the present invention to provide a flexible synthesis of (+)-pilocarpine and its analogues from the readily available amino acid L-aspartic acid via several novel intermediates in commercially useful diastereomer ratios. One intermediate (known to the art) is a nitrogen protected aspartic acid diester of Formula I

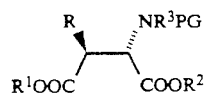

wherein R, $R^1$ and $R^2$ are each independently alkyl with 1 to 6 carbon atoms, cycloalkyl with 6 to 10 carbon atoms, aryl with 6 to 10 carbon atoms or arylalkyl with 7 to 19 carbon atoms, preferably n-alkyl with 1 to 6 carbon atoms, in particular 1 to 3 carbon atoms, $R^3$ is hydrogen or benzyl, PG is nitrogen-protecting group allowing deprotonation at the β-carbon of a protected aspartic acid diester and the α-carbon atoms has the S-configuration, R is preferably n-alkyl with 1 to 6 carbon atoms, in particular ethyl. The prior art preparation for the Formula I intermediate was described by Wolf and Rapoport in their 1989 article, supra, in which a diastereomer ration of 3.5:1 was achieved. However, one aspect of the present invention is the preferred preparation of the Formula I intermediate through kinetic control of the preparation so as to achieve almost quantitative amounts of the desired diastereomer. This kinetic control is achieved by manipulations of solvent polarity and diester concentrations.

The Formula I intermediate is converted into the intermediate of Formula IV

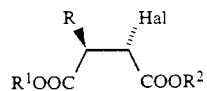

wherein R, $R^1$ and $R^2$ have the meaning given and Hal is a halogen, more particularly is chloride (Cl), bromide (Br) or iodine (I), which is in turn converted by a condensation reaction with an acyl-aryl derivative of Formula V

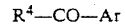

$R^4$—CO—Ar wherein Ar is a homo- or heteroaromatic ring with 5 to 6 ring atoms being optionally substituted by $C_{1-6}$ alkyl or alkoxy groups, halogen atoms, cyano or nitro groups and $R^4$ is H or $C_{1-6}$ alkyl to yield a diastereomeric mixture of cyclic lactones of Formula VIa and VIb

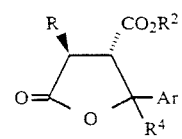

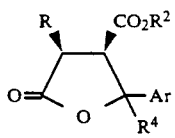  VIb

The desired diastereomer (that is, the lactone of Formula VIa) is easily separated and converted by hydrogenolysis and a reduction reaction to the optically active lactone of Formula VIII

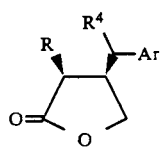  VIII

The product (wherein R is ethyl, $R^4$ is H and Ar is 1-methylimidazol-5-yl) is (+)-pilocarpine, which is well known to be therapeutically effective.

DETAILED DESCRIPTION OF THE PREFERRED EMBODIMENTS

Briefly, the present inventive synthesis lies in a conversion of L-aspartic acid into optically active lactones, which are analogues of (+)-pilocarpine. The invention therefore relates in particular to a method for preparing optically active lactone intermediates comprising the step of converting nitrogen-protected B-alkyl aspartic acid diester of Formula I,

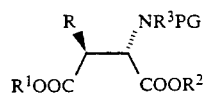  I wherein R, $R^1$ and $R^2$ are each independently alkyl with 1 to 6 carbon atoms, cycloalkyl with 6 to 10 carbon atoms, aryl with 6 to 10 carbon atoms or arylalkyl with 7 to 19 carbon atoms, preferably n-alkyl with 1 to 6, in particular 1 to 3 carbon atoms, $R^3$ is hydrogen or benzyl, preferably hydrogen, PG is a nitrogen-protecting group allowing deprotonation at the β-carbon without deprotonation at the α-carbon of a protected aspartic acid diester, preferably 9-(H)-fluorenyl, 9-(H)-9-phenylfluorenyl or trityl, in particular 9-(H)-9-phenylfluorenyl and the β-carbon atom has the S-configuration, into an optically active half-ester of the Formula II,

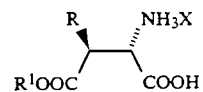  II wherein R and $R^1$ have the meaning given and X denotes Cl or Br, by removing the protecting group and hydrolysis using copper(II) salts. The inventive method further comprises converting the half-ester of Formula II by reacting it with a nitrosylation agent in the presence of a hydrogen halide, preferably sodium nitrite in the presence of hydrogen bromide, into a halogen compound of the Formula III,

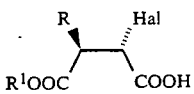  III wherein Hal denotes Cl, Br or I and the α-carbon atom and the β-carbon atom have the S-configuration. The inventive method yet further comprises:

(a) esterifying the compound of the Formula III to yield a diester of the Formula IV,

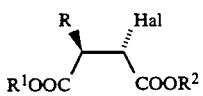  IV wherein R, $R^1$, Hal have the meaning given and $R^2$ being preferably n-alkyl with 1 to 6 carbon atoms or tert-butyl, (b) reacting the compound of the Formula IV with a acyl-aryl derivative of the Formula V, $R^4$—CO—Ar   V wherein Ar is a homo- or heteroaromatic ring with 5 or 6 ring atoms being optionally substituted by $C_{1-6}$ alkyl or alkoxy groups, halogen atoms, cyano or nitro groups, preferably phenyl, pyrrole, imidazole, thiadiazole, pyridine or pyrimidine, being optionally substituted by one, two or three $C_{1-4}$ alkyl or alkoxy groups, halogen atoms, cyano or nitro groups, in particular substituted imidazole preferably of the formula

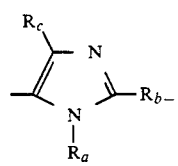

in which $R_a$, $R_b$ and $R_c$ are each independently H or n-alkyl with 1 to 4 C atom, most preferred 1-methylimidazole-5-yl, and $R^4$ is H or $C_{1-6}$ alkyl, preferably H or $C_{1-3}$ n-alkyl, under conditions of a condensation reaction to yield a diastereomeric mixture of lactones of the Formula VIa and VIb,

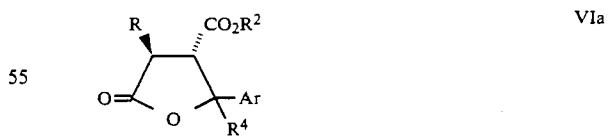  VIa

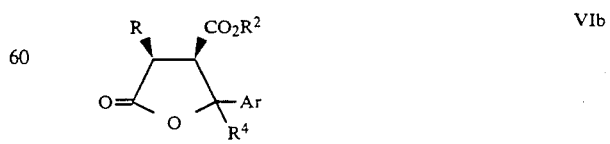  VIb wherein R, $R^2$, $R^4$ and Ar have the meanings given. The acyl-aryl derivatives are known or can be prepared analogously to methods that are known to the skilled worker, for example, Olah, G. A. in "Friedel-Crafts and Related Reactions", Interscience Publishers, New York 1963–1964 (R·H).

The formyl derivatives (R=H) can be obtained by VilsmeierHaack reaction, for example de Meheas, M., Bull. Soc. Chim. Fr. 1989-1999 (1962). The 1-alkyl-5-formylimidazoles can be prepared, for example, according the International Patent Application WO 89/09768.

The inventive method continues by including the isolation of the cyclic lactone of the Formula VIa by crystallization, followed by hydrogenating the lactone of the Formula VIa to yield a half-ester of Formula VII,

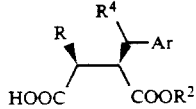

VII wherein R, $R^2$, $R^4$ and Ar have the meaning given, and the reduction of the half-ester of the Formula VII to yield the optically active lactone of the Formula VIII,

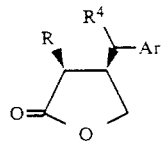

VIII wherein R, $R^4$ and Ar have the meanings given.

The invention moreover relates to method steps wherein one (a) hydrolyses the lactone of the Formula VIa to yield the carboxylic acid of the Formula IX,

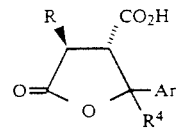

IX (b) reduces it to yield the alcohol of the Formula X,

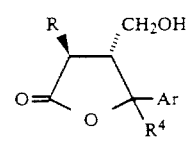

X wherein R, $R^4$ and Ar have the meanings given, and
(c) hydrogenates the alcohol of the Formula X to yield the optically active lactone of the Formula VIII.

Additionally the invention relates to a method comprising
(a) reacting the carboxylic acid of the formula IX with a metal organic compound of the Formula XI, Met-$R^5$                                                      XI wherein Met is Li, MgCl or MgBr and $R^5$ is $C_{1-6}$ alkyl, preferably $C_{1-3}$ n-alkyl, to yield a ketone of the Formula XII,

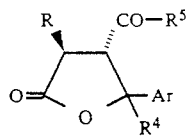

XII wherein R, $R^4$, $R^5$ and Ar have the meanings given.
(b) reducing the ketone of the Formula XII to yield an alcohol of the Formula XIII,

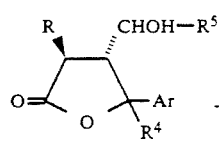

XIII and
(c) hydrogenates this alcohol to yield the optically active lactone of the Formula XIV,

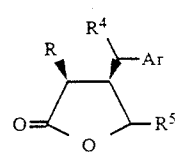

XIV wherein R, $R^4$, $R^5$ and Ar have the meanings given.

The invention furthermore relates to method steps of
(a) treating the alcohol of the Formula X (wherein $R^4$ is hydrogen) with an oxidizing agent to yield the ketone of the Formula XV

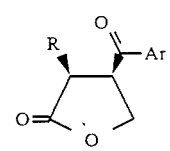

XV wherein R and Ar have the meanings given,
reacting it optionally with a metal organic compound of the formula XVI $R^4$-Met                                                      XVI wherein $R^4$ and Met have the meanings given, and
(c) treating it with a reducing agent to yield the optically active lactone of the formula VIII.

Moreover, the invention relates to a lactone intermediate of the Formula II,

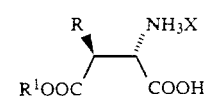

II wherein R, $R^1$ and X have the meanings given, a lactone intermediate of the Formula III,

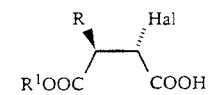

III wherein R, $R^1$ and Hal have the meanings given, a lactone intermediate of the Formula IV,

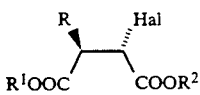

wherein R, R¹, R² and Hal have the meanings given, a lactone of the Formula VIa,

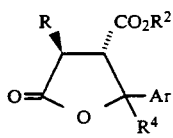

wherein R, R², R⁴ and Ar have the meanings given, in particular a lactone wherein R is ethyl, R² is $C_{1-6}$ alkyl, R⁴ is H, and Ar is 1-$C_{1-6}$-alkylimidazole-5-yl more particularly wherein Ar is 1-methyl-imidazole-5-yl, a half-ester of the Formula VII,

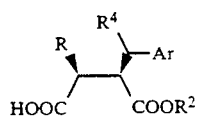

wherein R, R², R⁴ and Ar have the meanings given, in particular wherein R is ethyl, R² is $C_{1-6}$ alkyl, R⁴ is H, and Ar is 1-$C_{1-6}$-alkylimidazole-5-yl, more particularly 1-methylimidazol-5-yl, and to an alcohol of the Formula X already described, particularly wherein R is ethyl, R⁴ is H, and Ar is 1-methylimidazole-5-yl.

As may be seen, the diesters (that is R¹ and R²) of Formula I may be a wide variety of moieties; however, the nitrogen-protecting group is essential because it allows anion formation exclusively at the β-carbon. The preferred nitrogen-protecting group (that is, "PG") is a 9-phenyl-9H-fluorenyl group or a trityl group, preferably derived from a 9-phenyl-9-bromofluorene or from trityl bromide. By "S-configuration" (and later by the additional use of the phrase "R-configuration") is meant the means of designating absolute stereochemistry of an enantiomer by the Cahn-Ingold-Prelog system.

The conversion of the L-aspartic acid into the optically active, nitrogen-protected aspartic acid diester of Formula I may be achieved by several different paths. But in all paths, the nitrogen should be substituted with the nitrogen-protecting group in order to protect the chirality at the α-carbon while the β-carbon is ethylated.

The protection group PG is easily removed from the compound of Formula I by known process usually applied by the skilled worker, for example, to be found in Macomie, Protective Groups in Organic Chemistry, Plenum Press, New York, 1973.

The preferred 9-phenyl-9H-fluorenyl group is split off advantageously by hydrogenolysis, preferably in presence of a inorganic acid, in particular in the presence of hydrogen bromide. The hydrogenolysis can be carried out, for example, by catalytic hydrogenation at temperatures between about 0° C. and about 200° C. under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Advantageously suitable catalysts are noble metals, such as Pt or Pd, which can be used in the form of oxides (for example $PtO_2$ or PdO) on a support (for example Pd on charcoal, calcium carbonate or strontium carbonate), or in finely divided form. More preferred the hydrogenolysis is carried out in an alcohol with Pd on charcoal. The hydrogenolysis is advantageously carried out at temperature between about −50° C. and +150° C., in particular between 0° C. and 100° C. with a hydrogen pressure of about 15 to 100 psi, in particular 35 to 70 psi. At these reaction conditions, the reactions are as a rule ended after 30 minutes and 48 hours.

After the protecting group having been split off the resulting diester of β-alkyl aspartic acid of Formula Ia

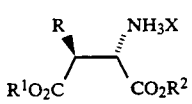

is selectively hydrolyzed using copper(II) salts. Hydrolytic reagents which are preferably used are copper(II) hydroxide, copper(II) sulfate, copper(II) carbonate, copper(II) acetate or mixtures thereof. Examples of suitable solvents for this hydrolysis reaction are water, alcohols, such as methanol or ethanol, amides, such as dimethylformamide, ethers, such as tetrahydrofuran or mixtures of those solvents, in particular mixtures of water and alcohols. In the hydrolysis reaction a chelate complex between the half-ester of Formula II and the copper ion is formed. In order to destroy this stable complex an agent is added that traps the copper ion. Preferred trapping agents are hydrogen sulfide, ethane-1,2-dithiole or propane-1,3-dithiole, or an ion exchange resin.

The half-ester of Formula II is converted into a halogen compound of Formula III using a nitrosylation agent in the presence of a hydrogen halide, preferably hydrogen bromide. Preferred nitrosylation agents are, for example, sodium nitrite or alkyl nitrites such as tert-butylnitrite. The reaction is carried out, for example, in an aqueous solution of the hydrogen halide at temperatures between −50° C. and 0° C. in particular −20° C. and 0° C. At these temperatures the reaction is, as a rule, ended after between 30 minutes and 10 hours.

The reaction of the halogen compound Formula III with alcohol of the formula R²OH can be carried out by the known customary methods for esterification such as are described, for example, in Houben-Weyl, Methoden der Organischen Chemie (Methods of Organic Chemistry). The reaction components are preferably reacted with the addition of a dehydrating agent, such as, for example, an acid (e.g. sulfuric acid, phosphoric acid, hydrochloric acid, or p-toluenesulfonic acid), an acid derivative (e.g. phosphorus pentoxide, phosphorus trichloride, phosphorus pentachloride, or phosphorus oxychloride), a metal salt (e.g. such as anhydrous calcium chloride, copper sulfate, or iron(III) chloride), an acid ion exchanger or molecular sieves. The water of reaction formed can also be removed by azeotropic distillation with a suitable solvent, such as benzene, toluene, chloroform or methylene chloride.

The condensation reaction between the diester of the Formula IV and the acyl aryl derivative of the Formula V can be carried out by the known customary methods for aldol condensation or Reformatsky reaction, such as are described, for example, in M. W. Rathke, Org. React. 22, 423–460 (1975); however, a particularly preferred component for use during the Reformatsky reaction is dimethylaluminum chloride.

The reaction components are preferably reacted with zinc, in particular a zinc-silver couple, in an inert solvent. Suitable inert solvents are ethers such as dioxane, tetrahydrofuran, diethylether or methyltert-butylether or hydrocarbons such as hexane, cyclohexane, benzene or toluene or mixtures thereof. Preferably the reaction is carried out in the presence of a copper(I) salt such as copper(I) chloride or copper(I) bromide and a dialkylaluminium halide, such as diethylaluminium chloride ($Et_2AlCl$), diisobutylaluminium chloride ( (i-$Bu_2$) AlCl) or dimethylaluminium chloride ($Me_2AlCl$), but most preferably $Me_2AlCl$, a dialkylboron triflate, such as dibutylboron triflate ((nBu)$_2$BTf), or a trialkylsilyl triflate, such as tert-butyldimethylsilyl triflate (But(Me)$_2$.SiTf). The reaction is carried out, for example, at temperatures between $-100°$ C. and $100°$ C., preferably $-20°$ C. and $+35°$ C. At these temperatures the reaction is, as a rule, ended after between 30 minutes and 30 hrs. The condensation reaction yields a diastereomeric mixture of the lactones of Formulae VIa and VIb. The desired diastereomer VIa is obtained in excess and the "wrong" diastereomer is separated easily by chromatography.

The diastereomer of Formula VIa is hydrogenated by catalytic hydrogenation at temperatures between about 0° C. and 200° C., preferably between 0° C. and 100° C., in particular between 10° C. and 50° C., under pressures between about 1 and 200 bar, in an inert solvent, for example an alcohol, such as methanol, ethanol, isopropanol, an ether, such as tetrahydrofuran (THF) or dioxane, carboxylic ester, such as ethyl acetate, a carboxylic acid such as acetic acid or mixtures of those solvents. Preferably the hydrogenation reaction is carried out in an alcohol, in particular in methanol. Advantageously suitable catalysts are noble metals such as Pt or Pd, which can be used in form of their oxides of hydroxides (for example PdO, Pd(OH)$_2$ or PtO$_2$) on a support (for example Pd on charcoal, calcium carbonate or strontium carbonate), or in finely divided form. The hydrogenation may also be carried out by heating with ammonium formate in methyl alcohol in the presence of Pd on charcoal. Such transfer hydrolysis (with ammonium formate and reflux) is faster than the first described process, but clean up may be more difficult.

The resulting half-ester of Formula VII is treated by a reducing agent, preferably a complex metal hydride. Reduction with complex hydrides, such as, for example, boranes (e.g. diborane, sodium or potassium or lithium boranate, a lithium cyano-trihydro-borate), metal hydrides (e.g. sodium hydride or aluminum hydride), silicon hydrides, (e.g. triethylsilane, tributyl-tin hydride), and mixed hydrides (e.g. lithium alanate, sodium alanate, diisobutyl-aluminum hydride or sodium bis(2-methoxyethxy)dihydroaluminate) where a mixed hydride is preferred. The reducing agent reduces the alkoxycarbonyl group to a hydroxy methyl group which, in situ, is intramolecularly esterified by the carboxyl group to yield the lactone ring.

Furthermore the lactone of Formula VIa can be thermically hydrolyzed, in particular when $R^2$ is a tertbutyl group, without loss of chirality using strong organic or inorganic acids, in particular trifluroacetic acid.

The resulting carboxylic acid of Formula IX can be reduced using complex hydrides, in particular diborane or sodium boranate (after the carboxylic acid group has been transformed to a carbonyl chloride) to yield the hydroxy methyl compound of Formula X, which gives the lactone of Formula VIII by catalytic hydrogenation.

The lactones being alkylated in the 4-position of Formula XIV can be obtained from carboxylic acid of Formula IX by reacting it with a metal organic compound of Formula XI. The reaction is advantageously carried out in an inert solvent. Preferred suitable inert solvents are ethers, such as diethyl ether, ethylene glycol dimethyl ether, tetrahydrofuran or dioxane, and amides, such as dimethylformamide, hexamethylphosphoric acid triamide, dimethylacetamide or N-methylpyrrolidone, and furthermore sulfoxides, such as dimethylsulfoxide or sulfolane, as well as hydrocarbons, such as pentane, hexane, cyclohexane, benzene or toluene or mixtures thereof. The reaction temperatures are advantageously between about $+40°$ C. and about $-100°$ C., preferably between $-80°$ C. and $+20°$ C., depending on the reactivity of the metal organic compound, and the reaction times are between 1 and 48 hours.

The resulting ketone is reduced, for example, with a complex hydride. Reduction with complex hydrides, such as, for example, boranes, such as diborane, sodium boranate or lithium cyano-trihydroborate, metal hydrides, such as sodium hydride or aluminum hydride, silicon hydrides, such as triethylsilane, tributyl-tin hydride and mixed hydrides, such as lithium alanate, sodium alanate or sodium his (2-methoxyethoxy)-dihydridoaluminate, or potassium boranate or lithium boranate is preferred.

The resulting alcohol is hydrogenated using the hydrogenation conditions as described for Formula VII to yield XIV.

Illustrative means of converting L-aspartic acid into the optically-active, nitrogen-protected aspartic acid diester of Formula I will now be described, followed by examples of different aspects of the invention leading to the ultimate synthesis of (+)-pilocarpine.

Example 1

L-Aspartic acid dimethyl ester hydrochloride

To a stirred suspension of L-aspartic acid (100.9 g, 758.0 mmol) in methanol (560.0 mL) was added thionyl chloride (125.0 g, 1050.7 mmol, 76.6 mL) dropwise over a 1 h period with ice cooling bath. After the addition was complete the ice bath was removed and the resulting clear solution was stirred for 40 h. The solvent was removed under reduced pressure and the residue was solidified by trituration with diethyl ether (100 mL). The solid was filtered, washed with cold ether and dried under vacuum to provide the dimethyl L-aspartate hydrochloride (150.5 g, 100%) which is pure enough for further reaction. The aspartate hydrochloride can be further crystallized from acetone (128.1 g, 85.1%) when a high quality sample is needed.

Yield: 100%.
Mp: 115–116° C.
$[\alpha]^{22}D$: $+6.0°$ (c=1.0 in $H_2O$).
Analogously are obtained:
L-aspartic acid diethyl ester hydrochloride.
L-aspartic acid dipropyl ester hydrochloride.

Example 2

N-(9-Phenylfluorenyl)-aspartic acid dimethyl ester

To a stirred suspension of anhydrous Pb(NO$_3$)$_2$ (45.0 g, 138.7 mmol) and anhydrous K$_3$PO$_4$ (75.0 g, 353.3 mmol) in dry acetonitrile (300.0 mL) was added sequentially L-aspartic acid dimethyl ester hydrochloride of Example 1 (32.0, 161.9 mmol) and 9-bromo-9-phenylfluorene (62.0 g, 193.2 mmol). The mixture which resulted was stirred for 20 h at room temperature and then filtered through celite. The filter cake was washed with chloroform (3×300.0 mL). The combined organic solvents were removed under reduced pressure and the residue oil was partitioned between ether (800.0 mL) and the solution of citric acid (5%, 200.0 mL). The ether layer was removed and the aqueous phase extracted with ether (3×200.0 mL). The combined organic layers were washed with brine (2×150.0 mL), dried (MgSO4) and then removed under reduced pressure. The residue was purified by a flash chromatograph (600.0 g silica gel, EtOAc/hexane, 1/10 to ½) to provide the product as a pale yellow oil (64.0 g).

Yield: 98.5%.

$[\alpha]^{22}D$: −232.2° C. (c=1.0 in CH3OH).

Analogously are obtained:

N-benzyl aspartic acid dimethyl ester.

N-trityl aspartic acid dimethyl ester.

Example 3

Dimethyl N-benzyl N-(9-phenylfluorenyl)-aspartate

To a stirred suspension of 14.6 g (50.7 mmol) L-N-benzylaspartic acid dimethyl ester hydrochloride (obtained by a reductive alkylation of the amino acid with benzaldehyde) in 80 ml dry CH3CN was added 13.8 g (41.7 mmol) anhydrous Pb (NO3)2 and 22.2 g (105 mmol) anhydrous K3PO4 followed by 20.5 g (63.5 mmol) 9-bromo-9-phenylfluorene in 40 ml CH3CN at RT under N2. The white suspension was stirred for 24 hours, then the reaction mixture was filtered through celite and the inorganic residue was washed with CHCl3. The combined organic layer was evaporated and the residue was partitioned between 200 ml aqueous 5% citric acid and 400 ml Et2O. The organic layer was dried (MgSO4) and evaporated. The thick yellow residue was purified by MPLC (Kieselgel, Hexane/EtOAc, 8:1) to leave the desired Formula I product as a pale yellow thick syrup. $C_{32}H_{29}NO_4$-491.53. Calc.: C, 78.18; H, 5.94; N, 2.85.

Example 4

(2S, 3S)-Dimethyl-N-(9-phenylfluorenyl)-3-ethylaspartate

To a stirred solution of dimethyl-N-(9-phenylfluorenyl)aspartate of Example 2 (63.0 g, 157.1 mmol) in THF (700.0 mL), cooled to −74° C. by a dry ice/isopropanol bath, was added a solution of potassium bis(trimethylsilyl)amide (KHMDS) in toluene (0.6M, 270.0 mL) over a 45 min period.

The brown solution which resulted was stirred for additional 45 min at −74° C. and then ethyl trifluoromethanesulfonate (24.0 mL, 185.2 mmol) was added in one portion. The solution was stirred for 10 min at −71° C. and then warmed up to room temperature. Phosphoric acid (1M, 250.0 mL) was added and the aqueous phase was extracted with ether (3×300.0 mL). The combined organic layers were washed with brine (2×200.0 mL), dried (MgSO4), and then removed under reduced pressure. The residue was crystallized from methanol (200.0 mL) to provide the product (58.3 g) in diastereomeric ratio of 98.4/1.6.

Yield: 86.5%.

Mp: 138–139° C.

$[\alpha]^{22}D$: −302.2° (c=1.0 in CHCl3).

Analogously are obtained:

(2S,3S)-dimethyl-N-(9-phenylfluorenyl)-3-methylaspartate.

(2S,3S)-dimethyl-N-(9-phenylfluorenyl)-3-propylaspartate.

(2S,3S)-dimethyl-N-(9-phenylfluorenyl)-3-butylaspartate.

As can be seen from the just described data, the achieved diastereomeric ratio of 98.4:1.6 means that the desired diastereomer was obtained almost stereospecifically. This is in contrast to the about 3.5:1 stereoisometric raio for obtaining "compound 28" described by Wolf and Rapoport in the earlier cited 1989 article. By contrast to this prior art method, the Example 4 procedure just described had a ratio of solvents (THF:toluene) of 2.5:1 rather 8:1 of the earlier Wolf and Rapoport article. This means that the solvent in which the procedure was conducted was considerably less polar. Further, the amount of diester used was about 0.16M by contrast to the earlier described about 0.05M diester. Also, the Example 4 inventive method step had the base added to the ester. One or more of these differences permitted us to achieve kinetic control over this key preparation of the Formula I intermediate and gave a commercially usable ratio (almost quantitative) of the diastereomer.

Example 5

Dimethyl 3-ethyl-N-benzyl-N-(9-phenylfluorenyl)-aspartate

To a stirred solution of 8.65 ml (5.2 mmol) KHMDS (0.6M solution in toluene) in 50 ml dry THF was added 1.96 g (4.0 mmol) of dimethyl N-benzyl-N-(9-phenylfluorenyl)-aspartate of Example 3 dissolved in 8 ml THF drop by drop at −74° C. under N2. The pale yellow solution was stirred at −74° C. for 45 minutes then 568 μl (4.4 mmol) EtOTf were added neat at once at −76° C. After 10 minutes the reaction was quenched with 3 ml MeOH and partitioned between 40 ml 1M H3PO4 and 50 ml Et2O. The water layer was extracted with 40 ml Et2O and the combined organic layers were dried (MgSO4) and evaporated. The residue was purified by flash-chromatography (Kieselgel, Hexane/EtAc 8:1) to yield a mixture of dimethyl 3-ethyl N-benzyl-N-(9-phenylfluorenyl)-aspartate (20:1 mixture of diastereomers). The diastereomers were separated by MPLC (Kieselgel, Hexane/EtOAc 15:1) to yield the desired compound.

Example 6

(2S, 3S)-Dimethyl-3-ethyl-aspartate hydrobromide

A suspension of (2S,3S)-dimethyl-N-(9-phenylfluorenyl()-3-ethyl-aspartate of Example 4 (25.1 g, 58.5 mmol) in methanol (450 mL) was saturated with nitrogen for 10 minutes. To this suspension was added Pd/C (10%, 5.2 g) and a solution of hydrobromic acid in acetic acid (1:2, 35 mL). This mixture was hydrogenated at 55 psi for 4.5 h using a Parr hydrogenator. The reaction mixture was filtered through celite and the filter cake was washed with methanol (3×200 mL). The combined filtrate and washings were concentrated in vacuo to provide the crude product (27.2 g) which was used for next reaction without purification.

Analogously are obtained:

(2S,3S)-dimethyl-3-methyl-aspartate hydrobromide.

(2S,3S)-dimethyl-3-propyl-aspartate hydrobromide.

(2S,3S)-diethyl-3-ethyl-aspartate hydrobromide.
(2S,3S)-diethyl-3-methyl-aspartate hydrobromide.
(2S,3S)-diethyl-3-propyl-aspartate hydrobromide
(2S,3S)-dipropyl-3-ethyl-aspartate hydrobromide

Example 7

(2S, 3S)-2-Amino-3-(methoxycarbonyl)pentanoic acid hydrobromide

The crude material of (2S,3S)-dimethyl-3-ethylaspartate hydrobromide (27.2 g) of Example 6 was suspended in water (200.0 mL) and filtered. The filter cake was washed with water (300.0 mL) 2nd the combined aqueous solution were diluted with methanol (500.0 mL). To this solution was added copper(II) carbonate copper(II) hydroxide (76.4 g, 345.5 mmol) and the resulting green suspension was mechanically stirred in a Morton flask (2.0 L) for 119 h. The suspension was saturated with hydrogen sulfide for 1 h, then the resulting black suspension was filtered through celite. The filter cake was washed with an aqueous solution of methanol (70%, 1800.0 mL). The combined filtrate and washings were concentrated in vacuo to give the amino acid salt (19.6 g) which was used for further reaction without purification.

H NMR ($D_2O$): $\delta$ 0.76 (t, J=7.4 Hz, 3H, $CH_3$), 1.38–1.48 (m, 1H, $CH_2$), 1.54–1.65 (m, 1H, $CH_2$), 2.78 (dd, J=9.8, 5.0 Hz, 1H, CCH), 3.56 (s, 3H, $OCH_3$), 3.92 (d, J=4.9 Hz, 1H, NCH).

Analogously are obtained:
(2S,3S)-2-amino-3-(methoxycarbonyl)butyric acid hydrobromide.
(2S,3S)-2-amino-3-(methoxycarbonyl)hexanoic acid hydrobromide.
(2S,3S)-2-amino-3-(methoxycarbonyl) heptanoic acid hydrobromide.
(2S, 3S)-2-amino-3-(ethoxycarbonyl) pentanoic acid hydrobromide.

Example 8

(2S, 3S)-2-Bromo-3-(methoxycarbonyl)pentanoic acid

To a stirred suspension of crude amino acid salt (2S,3S)-2-amino-3-(methoxycarbonyl)pentanoic acid hydrobromide (19.6 g) of Example 7 in aqueous hydrobromic acid (2.5N), cooled to −9° C. with an ice water-salt-acetone bath, was added sodium nitrite (10.0 g, 144.9 mmol) in small portions over a 1.5 h period, keeping the internal temperature (measured by electronic internal temperature probe) below −7° C. The reaction mixture was stirred for 2 h in the cooling bath after the addition was complete, then it was extracted with ethyl acetate (2×500 mL). The combined organic layers were washed with saturated aqueous sodium chloride (2×250 mL), dried ($MgSO_4$), and concentrated in vacuo to give the bromoacid which slowly solidified to a waxy solid ( 13.0 g).

Yield: 93 % from (2S, 3S)-dimethyl-N-(9-phenylfluorenyl)-3-ethylaspartate (of Example 4).

$^{13}CNMR$ ($CDCl_3$): $\delta$ 9.80 (q), 22.77 (t), 44.11 (d), 49.00 (d), 52.28 (q), 172.90 (s), 174,57 (s)

Anal. Calcd. for $C_7H_{11}BrO_4$: C, 35.2; H, 4.6.
Found: C, 35.5; H, 4.7.

Analogously are obtained:
(2S,3S)-2-bromo-3-(methoxycarbonyl)butyric acid.
(2S,3S)-2-bromo-3-(methoxycarbonyl)hexanoic acid.
(2S,3S)-2-bromo-3-(methoxycarbonyl)heptanoic acid.
(2S,3S)-2-bromo-3-(ethoxycarbonyl)pentanoic acid.

Example 9

(2S, 3S)-Dimethyl-2-bromo-3-ethylsuccinate

To a solution of (2S,3S)-2-bromo-3-(methoxycarbonyl)pentanoic acid (11.0 g, 46.0 mM) of Example 8 in methanol (200.0 mL) was added sulfuric acid (5.0 mL). The solution which resulted was heated under reflux for 6 h. The reaction mixture was cooled to room temperature and the solvent was removed under reduced pressure. The residue was partitioned between diethyl ether (300.0 mL) and water (100.0 mL), and the layers were separated. The aqueous phase was extracted with ether (2×200.0 mL) and the combined ether layers were washed with cold aqueous sodium carbonate (10%, 2×30.0 mL), brine (2×50.0 mL), treated with activated carbon, filtered and dried ($Na_2SO_4$). The solvent was removed under reduced pressure and the residue was dried in vacuo to provide the product as a colorless oil (10.6 g, 91%). The analytical sample was obtained by a flash chromatograph on silica gel (EtOAc/hexane: 1/12).

Yield: 91%.
$[\alpha]^{22}D$ −72.4° C. (c=3.0 in $CHCl_3$).

Analogously are obtained:
(2S,3S)-diethyl-2-bromo-3-ethylsuccinate.
(2S,3S)-dimethyl-2-bromo-3-methylsuccinate.
(2S,3S)-dimethyl-2-bromo-3-propylsuccinate.
(2S,3S)-dimethyl-2-bromo-3-butylsuccinate.

Example 10

(2S, 3S)-2-Bromo-3-ethyl-1, 4-butanedioic acid 1-tertbutyl-4-methyl diester

To a frozen solution of 1.40 g (5.86 mmol) of (2S,3S)-2-bromo-3-(methoxycarbonyl)pentanoic acid of Example 8 and 2.0 ml of dry t-butanol in 2.0 ml of dry dioxane in a Fisher-Porter bottle, cooled in a dry ice-isopropanol bath, was added 20 ml of liquid isobutylene which was precondensed into a graduated cylinder cooled in a dry ice-isopropanol bath. To the resulting two-phase system was added 1.0 mL of concentrated sulfuric acid and the reaction vessel was sealed and shaken for 17.5 hours using a platform shaking apparatus. The vessel was cooled in a dry ice-isopropanol bath, opened carefully and the reaction mixture partitioned between 150 mL of diethyl ether and 70 mL of water. The layers were separated and the aqueous phase was extracted with 100 mL of ether. The combined organic layer were washed with 100 mL of saturated aqueous sodium chloride, dried ($MgSO_4$) and concentrated in vacuo to give 5.84 g of a yellow liquid. This material was chromatographed over 100 g of silica gel (ethyl acetate-hexane, 1:15) to give 1.57 g (91%) of the diester.

$^{13}C$-NMR ($CDCl_3$): $\delta$ 10.01 (q), 22.97 (t), 27.56 (q), 46.62 (d), 49.59 (d), 51.89 (q), 82.44 (s), 168.21 (s), 172.73 (s).

Example 11

(3S, 4RS, 5RS)-3-Ethyl-4-(methoxycarbonyl)-5-methylimidazol-5-yl) dihydro-2(3H)-furanone (VIa and VIb)

To a stirred suspension of zinc-silver couple (1380.0 mg) and copper(I) bromide (276.3 mg) in THF (30 mL, dry) was added the solution of dimethylaluminum chloride in hexane 81M, 16.7 mL) at room temperature. The suspension which resulted was stirred for 20 min at room temperature and then cooled to −8° C. A solution of (2S,3S)-dimethyl-2-bromo-3-ethylsuccinate (1530.0 mg, 13.9 mmol) of Example 9 in THF (30 mL) was added to the suspension over a 20 min period. The resulting black suspension was stirred for 2 hours at $-8°$ C. and then stirred for additional 30 min at room temperature. The reaction mixture was cooled to $-8°$ C. and then methanol/water (20 mL, 4:1) was very slowly added into the flask. The mixture was stirred for 20 min at room temperature and then filtered through celite.

The filter cake was washed with methanol (500 mL), methanolhydrochloric acid (20 mL, 10:1). The combined filtrate and washings were concentrated in vacuo to give a pale yellow foam (5040.0 mg). The residue was dissolved in aqueous phosphoric acid (1M, 100 mL), and the aqueous layer was washed with diethyl ether ($2 \times 50$ mL), while solid sodium carbonate was added in small portions until gas evolution ceased. The aqueous layer was saturated with solid sodium chloride and the layers were separated. The aqueous phase was extracted with ethyl acetate ($2 \times 150$ mL) and the combined organic layers were washed with saturated sodium chloride ($2 \times 50$ mL), dried ($MgSO_4$) and concentrated in vacuo to give an oil (3298.0 mg). The analytical sample was provided by silica gel chromatography (chloroform-isopropanol, 10:1).

Yield: 94%.

$^1$H NMR (CDCl$_3$): VIa: $\delta$ 0.95 (t, J=7.5 Hz, 3H, CH$_3$), 1.66–1.74 (m, 1H, CH$_2$), 1.78–1.94 (m, 1H, CH), 2.97 (ddd, J=5.2, 7.4, 11.1 Hz, 1H, CH), 3.33 (dd, J=9.8, 11.1 Hz, 1H, CH), 3.60 (s, 3H, CH$_3$), 3.66 (s, 3H, CH.), 5.39 (d, J=9.8 Hz, 1H, CH), 7.06 (s, 1H, CH), 7.43 (s, 1H, CH).

VIa: $\delta$ 0.95 (t, J=7.5 Hz, 3H, CH$_3$), 1.66–1.74 (m, 1H, CH$_2$), 1.78–1.94 (m, 1H, CH$_2$), 3.13 (dr, J=6.2, 10.1 Hz, 1H, CH), 3.47 (s, 3H, CH$_3$), 3.49 (t, J=8.9, 10.1 Hz, 1H, CH), 3.58 (s, 3H, CH$_3$), 5.68 (d, J=8.9 Hz, 1H, CH), 6.91 (s, 1H, CH), 7.34 (s, 1H, CH).

VIb: $\delta$ 1.01 (t, J=7.5 Hz, 3H, CH$_3$), 3.62 (s, 3H, CH$_3$), 3.68 (s, 3H, CH$_3$), 5.60 (d, J=6.3 Hz, 1H, CH). Other proton signals of VIb were buried in the signals of VIa and not able to be distinguished.

Diast. Ratio: VIa/VIb: 91/9.

Anal. Calcd for C$_{12}$H$_{16}$N$_2$O$_4$: C, 57.1; H, 6.4; N, 11.1. Found: C, 56.9; H, 6.3; N, 10.9.

Analogously are obtained:
(3S,4RS,5RS)-3-ethyl-4-(methoxycarbonyl)-5-phenyldihydro-2(3H)-furanone.
(3S,4RS,5RS)-3-methyl-4-(methoxycarbonyl)-5-(1-methylimidazol-5-yl)dihydro-2(3H)-furanone

TABLE I

"Aldol" Condensation at Different Conditions

| Entry | R$^2$ | Reagents | Solvents | Temperature | Time | Yield (%) |
|---|---|---|---|---|---|---|
| 1 | But | Zn, BrCH$_2$CH$_2$Br | Dioxane/n-Bu$_3$P | 90–95° C. | 2 h | 49 |
| 2 | But | Zn, BrCH$_2$CH$_2$Br | n-Bu$_3$P | 105–110° C. | 1.5 h | 25 |
| 3 | Me | Zn, BrCH$_2$CH$_2$Br | Dioxane/n-Bu$_3$P | 90–95° C. | 2 h | 35 |
| 4 | Me | Zn—Ag, Et$_2$AlCl | THF-Hexane | 25° C. | 1.5 h | 96 |
| 5 | But | Zn—Ag, Et$_2$AlCl | THF-Hexane | 25° C. | 1.5 h | 97 |

TABLE II

The Effects of the Enolating Agents on the Diastereoselectivity of the "Aldol" Condensation

| Entry | Enolating Agents | Conditions | Ratio of VIa/VIb | Yield |
|---|---|---|---|---|
| 1 | Zn—Ag, Et$_2$AlCl | 22° C., 1.5 h | 78:22 | 96 |
| 2 | Zn—Ag, (i-Bu)$_2$AlCl | 22° C., 1.5 h | 63:37 | 70 |
| 3 | Zn—Ag, Me$_2$AlCl | 22° C., 1.0 h | 90:10 | 95 |
| 4 | Zn—Ag, (n-Bu)$_2$BTf | 0° C., 16 h | 75:25 | 30 |
| 5 | Zn—Ag, But(Me)$_2$SiTf | 22° C., 8.0 h | — | — |

Thus, as can be seen from the Table II data, the use of the Me$_2$AlCl under the "entry 3" conditions provided a ratio of 90:10 for the Formula VIa/VIb lactones with a yield of 95%. It is for this reason that the Reformatsky (sometimes also described as the "Aldol" condensation) utilizes dimethylaluminum chloride because the desired diastereomer of Formula VIa is obtained in a ratio approaching quantitative.

TABLE III

The Effects of the Temperature on the Diastereoselectivity of the "Aldol" Condensation

| Entry | Enolating Agents | Conditions | Ratio of VIa/VIb | Yield |
|---|---|---|---|---|
| 1 | Zn—Ag, Et$_2$AlCl | 22° C., 1.5 h | 78/22 | 96 |
| 2 | Zn—Ag, Et$_2$AlCl | −6° C., 17 h | 84/16 | 90 |
| 3 | Zn—Ag, Et$_2$AlCl | −76° C., 17 h | 84/16 | 88 |
| 4 | Zn—Ag, Me$_2$AlCl | 22° C., 1 h | 90/10 | 95 |
| 5 | Zn—Ag, Me$_2$AlCl | −20° C., 3 h | 91/9 | 96 |
| 6 | Zn—Ag, Me$_2$AlCl | −60° C., 3 h | 92/8 | 97 |

TABLE IV

The Effects of the Solvents on the Diastereoselectivity of the "Aldol" Condensation

| Entry | Enolating Agents | Solvents | Conditions | Ratio of VIa/VIb | Yield (%) |
|---|---|---|---|---|---|
| 1 | Zn—Ag, Me$_2$AlCl | Ether-Hexane (4.5/1) | −10° C. 1.5 h | — | — |
| 2 | Zn—Ag, Me$_2$AlCl | THF-Toluene (1/1) | −10° C. 1.5 h | 91/9 | 20 |
| 3 | Zn—Ag, Me$_2$AlCl | THF | −10° C. 45 min | 91/9 | 95 |
| 4 | Zn—Ag, Me$_2$AlCl | THF-Hexane | −10° C. 1.5 h | 91/9 | 94 |

Example 12

(3S, 4RS, 5RS)-3-Ethyl-4-(tert-butoxycarbonyl)-5-(methylimidazol-5-yl)-dihydro-2 (3H)-furanone To a stirred solution of 540 mg (8.26 mmol) of the zinc-silver couple and 110 mg (0.767 mmol) of copper(I) bromide in 13 mL of dry tetrahydrofuran was added 7 mL (7.00 mmol) of a 1.0M solution of diethylaluminum chloride in hexane. The resulting suspension was stirred for 1 hour, then a solution of 610 mg (5.55 mmol) of aldehyde 4 and 1.60 g (5.42 mmol) of (2S,3S)-2-bromo-3-ethyl-1,4-butanedioic acid 1-tert-butyl-4-methyl diester of Example 10 in 14 mL of tetrahydrofuran was added dropwise via syringe pump over a 75-minute period.

After the addition was complete, the resulting solution was stirred for 1.5 hours at room temperature, then it was cooled in an ice water bath. The reaction mixture was quenched with 5 mL of 50% aqueous methanol and 10 mL of ethyl acetate allowed to stir for 5 minutes, and the resulting gelatinous suspension was filtered through celite. The filter cake was washed with 200 mL of ethyl acetate and 150 ml of chloroform, then the combined filtrate and washings were concentrated in vacuo to give 2.49 g of a white foam.

The above material was dissolved in 75 mL of chloroform and this solution was extracted with three 75-mL portions of 1M aqueous phosphoric acid. The combined acid layers was washed with 200 mL of ethyl acetate, then the aqueous phase was vigorously stirred with 250 mL of ethyl acetate while solid potassium carbonate was added in small portions until gas evolution ceased. The aqueous phase was saturated with solid sodium chloride and the layers were separated. The aqueous phase was extracted with 250 mL of ethyl acetate while solid potassium carbonate was added in small portions until gas evolution ceased. The aqueous phase was saturated with solid sodium chloride and the layers were separated. The aqueous phase was extracted with 250 mL of ethyl acetate and the combined organic layers were washed with two 125-mL portions of saturated aqueous sodium chloride. The organic layer was dried (MgSO$_4$) and concentrated in vacuo to give 1.54 g (97%) of essentially pure lactone as a light yellow oil.

Example 13

(2S, 3R)-2-Ethyl-3-(methoxycarbonyl)-4-(1-methylimidazol-5-yl)-butyric acid

A solution of lactone VIa of Example 11 (1000.0 mg, 4.0 mmol) in methanol (20 mL) was saturated with nitrogen for 5 min. To this solution was added Pd/C (5%, 2000.0 ms) and the resulted suspension was shaken on a Parr hydrogenation apparatus under hydrogen (65 psi) for 60 h. The reaction mixture was filtered through celite and the filter cake was washed with methanol (300 mL). The combined filtrate and washings were concentrated in vacuo to give the acid (1008.0 mg).

Analogously are obtained:
(2S,3R)-2-methyl-3-(methoxycarbonyl)-4-(1-methylimidazol-5-yl)-butyric acid.
(2S,3R)-2-propyl-3-(methoxycarbonyl)-4-(1-methylimidazol-5-yl)-butyric acid.
(2S,3R)-2-ethyl-3-(ethoxycarbonyl)-4-(1-methylimidazol-5-yl)-butyric acid.
(2S,3R)-2-ethyl-3-(methoxycarbonyl)-4-phenyl-butyric acid.

TABLE V

| | | Hydrogenolysis of the Lactone VIa | | | | |
|---|---|---|---|---|---|---|
| Entry | Catalysts | H$_2$ (psi) | Solvents | Temperature (°C.) | Time (hr) | Yield |
| 1 | Pd/C (10%) | 60 | HAc/MeOH | 22 | 24 | 30% |
| 2 | Pd(OH)$_2$/C (20%) | 60 | MeOH | 22 | 24 | 40% |
| 3 | Pd/C (10%) | 60 | HAc/MeOH | 22 | 24 | — |
| 4 | Pd/C (10%) | 60 | MeOH | 22 | 48 | 100% |
| 5 | Pd/C (5%) | 60 | MeOH | 22 | 72 | 100% |

The just described procedures for hydrolysis of the desired lactone VIa could also, as earlier noted, be performed by use of ammonium formate with reflux. One would expect to achieve comparable results, which as noted, can be a 100% yield through choice of appropriate process conditions.

Example 14

(+)-Pilocarpine (VII)

To a stirred solution of (2S,3R)-2-ethyl-3-(methoxycarbonyl)4-(1-methylimidazol-5-yl)-butyricacid of Example 13 (1000.0 mg, 3.9mmol) in isopropanol (25.0 mL) was added lithium borohydride (43S.6 mg, 20.0 mmol) over a 10 min period at −5° C. The mixture was stirred for 1 h at −5° C., and then stirred for additional 21 h at room temperature. Methanol (8.0 mL) was added and the mixture which resulted was stirred for 30 min. Water (1.0 mL) was added, followed by concentrated hydrochloric acid to give pH=1. The solution which resulted was stirred at room temperature for 2 h and then concentrated in vacuo for 1 h at 60° C. The residue was dissolved in aqueous hydrochloric acid (1M, 10 mL). Solid sodium bicarbonate was added to the solution with stirring till pH=8 at 0° C. The aqueous layer was extracted with chloroform (3×100 mL). The combined organic extracts were dried (MgSO$_4$) and acidified with concentrated hydrochloric acid, and then concentrated in vacuo to give a residue (850.0 mg, 88%) which was crystallized from ethanol/acetone to provide the hydrochloride of (+)-pilocarpine (715.0 mg, 75%).

Yield:
(free base): 88% (+) -pilocarpine/(−)-isopilocarpine: 91/9.
(hydrochloride): 88% (+) -pilocarpine/(−)-isopilocarpine: 91/9.
(recrystallized): 75%, 98/2 .
Mp: 200–201° C. (lit.1 195–198° C. or 202–205° C.).
$^{13}$C NMR (CDCl$_3$): δ 12.14 (q), 18.22 (t), 21.25 (t), 31.29 (q), 37.17 (d), 44.77 (d), 69.79 (t), 126.88 (d), 128.55 8s), 138.22 (d), 177.85 (s).
[α]$^{22}$D: +88 (c=2 in H$_2$O) (lit. [α]$^{18}$D+91°).

[1]Merck Index, 10th Edition (1983), p. 1070, entry 7301.

Example 15

(3S, 4RS, 5RS)-3-Ethyl-4-(tert-butoxycarbonyl)-5-(1-methylimidazol-5-yl) -dihydro-2(3H)-furanone trifluoroacetate salt To a stirred solution of 1.79 g (6.09 mmol) of lactone t.-butyl ester of Example 12 in 20 mL of dichloromethane was added 10 mL (14.8 g; 130 mmol) of trifluoroacetic acid. The resulting solution was stirred for 18 hours, then concentrated in vacuo. The residual yellow oil was co-evaporated from a mixture of ethyl acetate and benzene several times to give 2.09 g (96%) of the lactone acid salt as a white solid: mp 112–114° C. Analysis of this mixture by 500 mHz $^1$H NMR (D$_2$O) indicates that this mixture is a 4.5:3.8:1.0 mixture of diastereomers. Anal. Calcd for C$_{13}$H$_{15}$F$_3$N$_2$O$_2$: C, 44.33; H, 4.29; N, 7.95. Found: C, 44.33; H, 4.39; N, 7.60.

Example 16

(3S, 4RS, 5RS)-3-Ethyl-4-(hydroxymethyl)-5-(1-methylimidazol-5-yl)-dihydro-2(3H)-furanone To a stirred suspension of 230 mg (0.679mmol) of acid salt of Example 15 in 2.4 mL of dry tetrahydrofuran, cooled in a dry ice-isopropanol bath, was added 3.4 mL (3.4 mmol) of a 1.0M THF solution of the borane-THF complex dropwise over a 30-minute period. The reaction mixture, which now had become homogenous, was stirred for an additional 30 minutes in the dry ice-isopropanol bath, then it was stirred for 2 hours in an ice water bath. Next, the reaction mixture was quenched by the dropwise addition of 10 mL of methanol over a 10-minute period, with ice bath cooling. The ice bath was removed after the addition was complete, and the resulting solution was stirred for 30 minutes, then concentrated in vacuo. The residue was co-evaporated with methanol several times, followed by co-evaporation with a mixture of methanol and benzene to give 198 mg of a colorless oil.

This oil was partitioned between 25 mL of 1M aqueous phosphoric acid and 30 mL of chloroform. The layers were separated and the organic phase was extracted with 25 mL of 1M phosphoric acid. The combined aqueous acid layers were washed with 50 mL or ethyl acetate, then the aqueous phase was vigorously stirred with 75 mL of ethyl acetate while solid potassium carbonate was added in small portions until CO$_2$ gas evolution ceased. The aqueous phase was saturated with solid sodium chloride and the layers were separated. The aqueous phase was extracted with 75 mL of ethyl acetate and the combined organic layers were washed with 75 mL of saturated sodium chloride, dried (MgSO$_4$) and concentrated in vacuo to give 87 (57%) of the hydroxymethyl lactone as a colorless, cloudy oil. Analysis of this product by 400MHz $^1$H NMR indicated a 3.1:1.9:1.0 ratio of isomers.

Example 17

(3S, 4RS, 5RS)-3-Ethyl-4-(hydroxymethyl)-5-(1-methylimidazol-5-yl)-dihydrofuran-2(3H)-furanone To a stirred suspension of 2.01 g (5.71 mmol) of lactone acid of Example 15 in 50 mL of dry dichloromethane was added 7 drops of dry dimethylformamide (DMF). This suspension was cooled in an ice water bath, then 12 mL (17.5 g; 138 mmol) of oxalyl chloride was added in one portion. The reaction mixture was stirred for 10 minutes in the ice bath, then for 4 hours at room temperature. The solvent and excess oxalyl chloride were removed in vacuo and the residue was dried by coevaporation from benzene. The crude acid chloride was dissolved in 25 mL of dry DMF and cooled in a dry ice-isopropanol bath. To this solution was added a solution of 900 mg (23.8 mmol) of sodium borohydride in 12 mL of dry DMF and the dry ice-isopropanol bath was replaced with a dry ice-carbon tetrachloride bath. The resulting semi-frozen mixture was stirred for 30 minutes in this bath, then it was stirred for 1.5 hours in an ice-salt-acetone bath. The reaction mixture was partitioned between 100 mL of ethyl acetate and 100 mL of 1M aqueous phosphoric acid. The layers were separated and the aqueous phase was washed with 100 mL of ethyl acetate, followed by two 100-mL portions of chloroform-isopropanol (9:1). The aqueous layer was vigorously stirred with 100 ml of chloroform-isopropanol (9:1) while solid potassium carbonate was added in small portions until gas evolution ceased. The aqueous phase was saturated with solid sodium chloride and the layers were separated. The aqueous layer was extracted with two 10-mL portions of chloroform-isopropanol (9:1) and the combined organic extracts were dried (MgSO$_4$) and concentrated in vacuo. The residue was chromatographed over 100 g of silica gel (chloroform-isopropanol, 1:1) to give 759 mg (59%) of the hydroxymethyl lactone as a pale yellow oil. 1H NMR (CDCl$_3$, 400 MHz; characteristic signals) δ 1.08 (t, J=7.5 Hz, 3H, CCH$_3$), 1.77–1.90 (m, 2H, CCH$_2$), 3.68 (s, 3H, NCH$_3$), 3.70 (s, 3H, NCH$_3$), 3.81–3.82 (m, 2H, CH$_2$O), 5.35 (d, J=9.2 Hz, 1H, ARCH), 5.67 (d, J=7.7 Hz, 1H, ArCH), 6.93 (s, 1H, NCH), 6.96 (s, 1H, NCH), 7.41 (s, 1H, NCH), 7.47 (s, 1H, NCH). The doublets at 5.35 and 5.67 ppm correspond to the major isomers of a 4.2:3.1:1.0 mixture of 3 products.

Example 18

(+)-Pilocarpine

A solution of 449 mg (2.00 mmol) of the 4-hydroxymethyl lactone of Example 16 in 25 mL of methanol was saturated with nitrogen for 15 minutes. To the resulting solution was added 2.25 g of 10% palladium-on-charcoal, followed by 2.56 g (40.5 mmol) of ammonium formate. The black suspension was stirred at room temperature for 10 minutes, then it was slowly heated to an oil bath temperature of 60–70° C. over a 30-minute period. The reaction mixture was kept at this temperature for 21 hours, cooled to room temperature, and filtered through celite. The filter cake was washed with 100 mL of methanol, then with 90 mL of a mixture of 2N aqueous hydrochloric acid in methanol (1:1). The combined filtrate and washings were concentrated in vacuo to give an orange solid which was dissolved in 45 mL of water and solid sodium bicarbonate was added until the solution was pH 8. This solution was extracted with 350-mL portions of chloroform and the combined organic layers were dried (MgSO$_4$) and concentrated in vacuo to give 234 g 856%) of (+)-pilocarpine and (−)-isopilocarpine as a pale yellow oil. The proton NMR of this material indicates a 6:1 ratio of (+)-pilocarpine to (−)-isopilocarpine.

It is to be understood that while the invention has been described above in conjunction with preferred specific embodiments, the description and examples are intended to illustrate and not limit the scope of the invention, which is defined by the scope of the appended claims.

It is claimed:

1. A method for preparing optically active lactone intermediates comprising the steps of:

converting nitrogen-protected β-alkyl aspartic acid diester of Formula I,

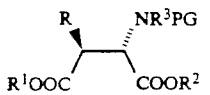

wherein R, $R^1$ and $R^2$ are each independently alkyl with 1 to 6 carbon atoms, cycloalkyl with 6 to 10 carbon atoms, aryl with 6 to 10 carbon atoms or arylalkyl with 7 to 19 carbon atoms, $R^3$ is hydrogen or benzyl, PG is a nitrogen-protecting group allowing deprotonation at the β-carbon without deprotonation at the α-carbon of a protected aspartic acid diester, and the β-carbon atom has the S-configuration, into an optically active halfester of the Formula II,

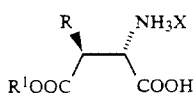

wherein R and $R^1$ have the meanings given and X denotes Cl or Br, by removing the protecting group and hydrolysis using copper(II) salts;

converting the half-ester of Formula II by reacting said half-ester with a nitrosylation agent in the presence of a hydrogen halide into a halogen compound of the Formula III,

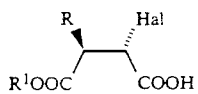

wherein Hal denotes Cl, Br or I and the α-carbon atom and the β-carbon atom each has the S-configuration;

esterifying the compound of the Formula III to yield a diester of the Formula IV,

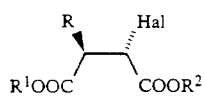

wherein R, $R^1$, $R^2$ and Hal have the meanings given; and reacting the compound of the Formula IV with a acyl-aryl derivative of the Formula V,

wherein Ar is phenyl, pyrrole, imidazole, thiadiazole, pyridine or pyrimidine, is connected through a ring carbon atom, and is optionally substituted by one, two or three $C_{1-4}$ alkyl or alkoxy groups, halogen atoms, cyano or nitro groups, and $R^4$ is H or $C_{1-6}$ alkyl, under conditions of a condensation reaction to yield a diastereomeric mixture of lactones of the Formulae VIa and VIb,

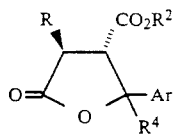

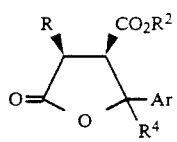

wherein R, $R^2$, $R^4$ and Ar have the meanings given.

2. The method according to claim 1 further comprising reacting the acyl-aryl derivative of the Formula V with the diester of the Formula IV in the presence of zinc.

3. The method according to claim 2 further comprising reacting the acyl-aryl derivative of the Formula V with the diester of the Formula IV in the presence of a zinc-silver couple.

4. The method according to claim 3 further comprising reacting the acyl-aryl derivative of the Formula V with the diester of the Formula IV in the presence of copper(I) salts.

5. The method according to claim 4 further comprising reacting the acyl-aryl derivative of the Formula V with the diester of the Formula IV in the presence of $C_{1-6}$ dialkylalumino halogenide.

6. The method according to claim 1 further comprising isolating the lactone of the Formula VIa by crystallization.

7. The method according to claim 6 further comprising (a) hydrolyzing the lactone of the Formula VIa to yield the carboxylic acid of the Formula IX,

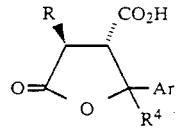

and
(b) reducing it to yield the alcohol of the Formula X,

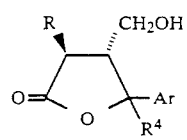

wherein R, $R^4$ and Ar have the meanings given.

8. The method according to claim 7 further comprising hydrogenating the alcohol of the Formula X to yield the optically active lactone of the Formula VIII,

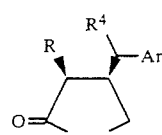

wherein R, $R^4$ and Ar have the meanings given.

9. The method according to claim 7 further comprising reacting the carboxylic acid of the formula IX with a metal organic compound of the Formula XI, Met-R$^5$      XI wherein Met is Li, MgCl or MgBr and R$^5$ is C$_{1-6}$ alkyl to yield a ketone of the Formula XII,

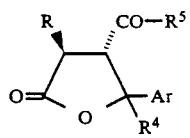      XII wherein R, R$^4$, R$^5$ and Ar have the meanings given.

10. The method according to claim 9 further comprising (a) reducing the ketone of the Formula XII to yield an alcohol of the Formula XIII,

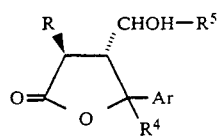      XIII and (b) hydrogenating this alcohol to yield the optically active lactone of the Formula XIV,

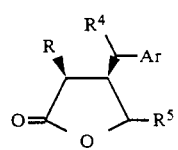      XIV wherein R, R$^4$, R$^5$ and Ar have the meanings given.

11. The method according to claim 7 further comprising (a) treating the alcohol of the Formula X (wherein R$^4$ is hydrogen) with an oxidizing agent to yield the ketone of the Formula XV

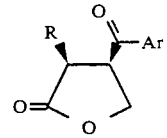      XV wherein R and Ar have the meanings given, (b) reacting said ketone optionally with a metal organic compound of the Formula XVI R$^4$-Met      XVI wherein R$^4$ and Met have the meanings given, and (c) treating said ketone of step (a) or step (b) with a reducing agent to yield the optically active lactone of the Formula VIII,

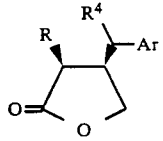      VIII wherein R, R$^4$ and Ar have the meanings given.

12. A lactone of the Formula VIa,

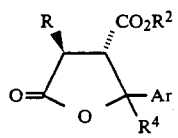      VIa wherein R is ethyl, R$^2$ is C$_{1-6}$ alkyl, R$^4$ is H, and Ar is phenyl, pyrrole, imidazole, thiadiazole, pyridine or pyrimidine, is connected through a ring carbon atom thereof, and is optionally substituted by one, two or three C$_{1-4}$ alkyl or alkoxy groups, halogen atoms, cyano or nitro groups.

13. A lactone according to claim 12, wherein R is ethyl, R$^2$ is C$_{1-6}$ alkyl, R$^4$ is H, and Ar is an unsubstituted or substituted imidazole-5-yl group of the formula

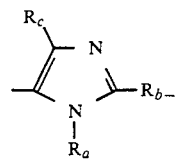

in which R$_a$, R$_b$, R$_c$ are each independently H or n-alkyl with 1 to 4 carbon atoms.

14. A cyclic lactone according to claim 13, wherein Ar is 1-methyl-imidazole-5-yl.

15. An alcohol of the Formula X,

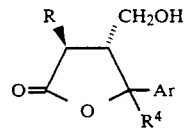      X wherein R is independently alkyl with 1 to 6 carbon atoms, cycloalkyl with 6 to 10 carbon atoms, aryl with 6 to 10 carbon atoms, or arylalkyl with 7 to 19 carbon atoms, R$^4$ is H or alkyl with 1 to 6 carbon atoms, and Ar is phenyl, pyrrole, imidazole, thiadiazole, pyridine or pyrimidine, is connected through a ring carbon atom, and is optionally substituted by alkyl or alkoxy groups with 1-6 carbon atoms, halogen atoms, cyano or nitro groups.

16. An alcohol according to claim 15, wherein R is ethyl, R$^4$ is H, and Ar is 1-methylimidazole-5-yl.

* * * * *

UNITED STATES PATENT AND TRADEMARK OFFICE
CERTIFICATE OF CORRECTION

PATENT NO. : 5,322,942
DATED : June 21, 1994
INVENTOR(S) : Henry Rapoport et al.

It is certified that error appears in the above-indentified patent and that said Letters Patent is hereby corrected as shown below:

In Column 24, the illustration in Claim 13
    replace 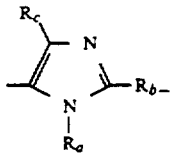

with 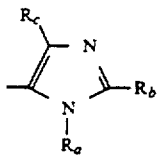

Signed and Sealed this

Third Day of January, 1995

*Attest:*

BRUCE LEHMAN

*Attesting Officer    Commissioner of Patents and Trademarks*